(12) United States Patent
Janssen

(10) Patent No.: US 11,992,328 B2
(45) Date of Patent: May 28, 2024

(54) BREAST PUMP DEVICE

(71) Applicant: KONINKLIJKE PHILIPS N.V., Eindhoven (NL)

(72) Inventor: Jozef Johannes Maria Janssen, Herten (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 517 days.

(21) Appl. No.: 17/019,438

(22) Filed: Sep. 14, 2020

(65) Prior Publication Data

US 2020/0405924 A1 Dec. 31, 2020

Related U.S. Application Data

(62) Division of application No. 15/753,382, filed as application No. PCT/EP2016/070785 on Sep. 3, 2016, now Pat. No. 10,806,836.

(30) Foreign Application Priority Data

Sep. 4, 2015 (EP) .................................... 15183876

(51) Int. Cl.
*A61M 1/06* (2006.01)
*A61B 5/00* (2006.01)

(52) U.S. Cl.
CPC ............. *A61B 5/4288* (2013.01); *A61M 1/06* (2013.01); *A61M 1/062* (2014.02);
(Continued)

(58) Field of Classification Search
CPC ....... A61B 5/4288; A61M 1/06; A61M 1/062; A61M 2205/18; A61M 2205/3306;
(Continued)

(56) References Cited

U.S. PATENT DOCUMENTS

| 6,315,955 B1 | 11/2001 | Klein |
| 6,471,660 B1 | 10/2002 | Covington |

(Continued)

FOREIGN PATENT DOCUMENTS

| EP | 1430918 | 6/2004 | |
| EP | 1430918 A1 * | 6/2004 | ........... A61B 5/4288 |

(Continued)

OTHER PUBLICATIONS

Daly, et al: "Degree of breast emptying explains change in the fat content, but not fatty acid composition, of human milk", Experimental Physiology, Cambridge University Press, Cambridge, GB, vol. 78, No. 6, Jan. 1, 1993, pp. 741-755.

(Continued)

*Primary Examiner* — Jason E Flick

(57) ABSTRACT

A single breast pump device (1) is adapted to enable realization of at least two batches (A, B) of breast milk as a direct result of a single pumping session to be performed on at least one user's breast, which batches (A, B) are different as far as the value of at least one quality parameter of the breast milk is concerned. The single breast pump device (1) comprises a detection unit (50) for performing real-time detection of the at least one quality parameter in a flow of breast milk and outputting a detection signal representing an actual value of the at least one quality parameter, and further comprises a controller (70) for receiving the detection signal from the detection unit (50) and using the signal in a process of determining an appropriate setting of the single breast pump device (1) as far as the choice of a destination position of the milk is concerned. A double breast pump device (2) is also disclosed.

20 Claims, 2 Drawing Sheets

(52) U.S. Cl.
CPC ..... *A61M 1/06935* (2021.05); *A61M 2205/18* (2013.01); *A61M 2205/3306* (2013.01); *A61M 2205/3313* (2013.01); *A61M 2205/3334* (2013.01); *A61M 2205/3337* (2013.01); *A61M 2205/50* (2013.01); *A61M 2205/502* (2013.01)

(58) Field of Classification Search
CPC .. A61M 2205/3313; A61M 2205/3334; A61M 2205/3337; A61M 2205/50; A61M 2205/502; A61M 2205/33; A61M 2205/3331
See application file for complete search history.

(56) References Cited

U.S. PATENT DOCUMENTS

| | | |
|---|---|---|
| 7,887,507 B2 | 2/2011 | Shemesh |
| 8,794,447 B2 | 8/2014 | Van Kasteren |
| 9,535,047 B2 | 1/2017 | Chen |
| 2009/0192367 A1 | 7/2009 | Braig |
| 2014/0263611 A1 | 9/2014 | Bauer |
| 2015/0265753 A1* | 9/2015 | Prentice ............... A61M 1/74 604/74 |
| 2016/0082165 A1* | 3/2016 | Alvarez ............... A61M 1/06 604/74 |

FOREIGN PATENT DOCUMENTS

| | | |
|---|---|---|
| EP | 2606816 | 6/2013 |
| WO | 2014058430 | 4/2014 |

OTHER PUBLICATIONS

Roman M. Balabin, Sergey V. Smirnov, "Melamine detection by mid- and near-infrared (MIR/NIR) spectroscopy: A quick and sensitive method for dairy products analysis including liquid milk, infant formula, and milk powder", Talanta, vol. 85, Issue 1, Jul. 15, 2011, pp. 562-568.

Jinying Yin et al., "Experimental Analysis on the Effect of Milk Fat Concentration on Light Scattering Intensity", (Abstract) ISSN: 0277-768X vol. 8686, 2013.

* cited by examiner

BREAST PUMP DEVICE

CROSS-REFERENCE TO RELATED APPLICATIONS

The present application is a Divisional Application under 37 C.F.R. § 1.53(b) of U.S. patent application Ser. No. 15/753,382 filed on Feb. 19, 2018, which is the U.S. National Phase application under 35 U.S.C. § 371 of International Application No. PCT/EP2016/070785, filed on Sep. 3, 2016, and which claims the benefit of European Application No. 15183876.0 filed on Sep. 4, 2015. Priority under 35 U.S.C. § 120 is claimed from U.S. patent application Ser. No. 15/753,382, and the entire disclosures of the prior applications are specifically incorporated herein by reference.

FIELD OF THE INVENTION

The invention relates to a breast pump device.

BACKGROUND OF THE INVENTION

Breast pump devices are well known devices for extracting milk from one or two breasts of a user. A breast pump device may be used if the baby or infant is not itself able to extract milk from the breast, or if the mother is separated from the baby or infant and is to be fed with breast milk by someone else. Hence, in general, breast pump devices are used by mothers to express breast milk at a convenient time, to be stored for later consumption by their child. A breast pump device may also be helpful in a situation in which it is desired to stimulate and increase milk production in women with a low milk supply.

A breast pump device is typically operated with at least one funnel-shaped element for receiving a user's breast, which may be equipped with pads or the like for massaging the breast in a certain way, and with at least one receptacle for receiving and containing breast milk, and comprises a pump such as a vacuum pump for creating underpressure in the funnel-shaped element so as to enable milk expression from the breast. The fact is that by generating a vacuum, possibly accompanied by a certain way of massaging the breast, a simulation of a feeding action is obtained, which triggers the necessary let-down reflex in the user of the breast pump device.

Normally, a receptacle is used per breast. Hence, when milk is simultaneously extracted from two breasts, which is a possibility offered by many available types of breast pump device, particularly electrically driven types, two receptacles are normally used, one receptacle for each breast. Assuming that a receptacle is large enough for receiving the entire volume extracted from a breast during a pumping session, the result of operation of the breast pump device is one or two receptacles containing the volume as mentioned.

In some cases, it is desirable to have breast milk with a relatively high milk fat concentration, or a relatively high value of another quality parameter of the breast milk such as the protein content. For example, when it comes to feeding preemies, it is advantageous to use breast milk which is high in fat and nutrients. However, the fact is that the currently known breast pump devices are only adapted to deliver one homogenous batch of milk per breast, as explained in the foregoing. In view thereof, there is a need for realizing a way of obtaining a separation of the entire volume extracted from a breast during a pumping session in at least two batches which are different as far as the value of at least one quality parameter of the breast milk is concerned.

EP 1 430 918 A1 relates to a system and to a process for detecting a milk surge in a mother's breast and to the use of a breast pump for detecting a milk surge. The milk is expressed into at least one collecting container, and the quantity of milk expressed is determined as a function of time. If a milk surge takes place, then the quantity of milk detected increases abruptly. It is thus easy to detect the milk surge. The quantity of milk is preferably weighed. Performing volume measurements is another example of a way to determine the quantity of milk expressed as a function of time.

Among other things, EP 1 430 918 A1 discloses a possibility of collecting the milk in several collecting containers, wherein the collecting containers are filled one after the other dependent on a predetermined event. Examples of this event include 1) a time period passed, which can always be the same or can change depending on the container to be filled, and 2) a predetermined quantity of milk collected in one of the containers. The milk collected in the several containers can be analyzed and also used individually, knowing that as milk is removed from the breast, the fat content of the milk increases.

SUMMARY OF THE INVENTION

It is an object of the invention to fulfill a need for realizing in an accurate manner a separation of an entire volume of extracted milk in at least two batches having different quality parameter values, such that it is possible to guarantee that at least one batch of milk meets predetermined quality requirements.

According to the invention, a breast pump device is provided, which is adapted to enable realization of at least two batches of breast milk as a direct result of a single pumping session to be performed on at least one user's breast, which batches are different as far as the value of at least one quality parameter of the breast milk is concerned, and which batches are realized at different destination positions, the device comprising a detection unit for performing real-time detection of the at least one quality parameter in a flow of breast milk extracted from the at least one user's breast during a pumping session, and outputting a detection signal representing an actual value of the at least one quality parameter, and a controller for receiving the detection signal from the detection unit, real-time determining a relation between the actual value of the at least one quality parameter and a reference value, and controlling the device on the basis of the relation as determined to direct the flow of breast milk to a destination position which is appropriate in view of the relation as determined.

It follows from the foregoing definition that the invention provides for real-time detection of at least one quality parameter of breast milk in a flow of the breast milk, and for real-time comparison of the actual value which is found in this way to a reference value, in order to be able to continuously determine a relation between the actual value and the reference value throughout a pumping session. The relation as determined indicates whether the breast milk meets certain predetermined quality requirements, or not, on the basis of which it is possible to choose an appropriate destination position of the milk, so that one batch of milk meeting the quality requirements and another batch of milk of another quality is are obtained. The invention is based on the insight that during a single pumping session, i.e. a single lactation process, quality parameters of the breast milk change over time. In particular, it is known that at the start of lactation, so-called foremilk is expressed by the breast during a limited period, followed by so-called hindmilk, an important difference between the two types of breast milk relating to the milk fat concentration, wherein the hindmilk has a considerably higher milk fat concentration than the foremilk. During a pumping session, it is practically impossible for a user to visually distinguish the hindmilk from the foremilk and to recognize the period during which the composition of the milk changes. When the invention is put to practice, the value of one or more quality parameters can automatically be determined, and this information can be used for determining if a flow of extracted milk should be directed towards a receptacle of milk which is expected to have a certain quality, or towards another destination position. The invention provides for a way of realizing a separation as desired during a pumping session, wherein there is no need for bothersome actions afterwards for achieving such a result, if such actions are available in practice at all.

In respect of the relation between the actual value of the at least one quality parameter and the reference value, it is noted that it may be found that the actual value is above the reference value, below the reference value, or the same as the reference value. In a practical embodiment, the controller is programmed with information regarding an appropriate setting of the device for each of the possible relations. For example, the content of such information may be that the device should be in a condition for directing the flow of breast milk to a destination position A when the actual value of the at least one quality parameter is above or equal to the reference value, and in a condition for directing the flow of breast milk to a destination position B when the actual value of the at least one quality parameter is below the reference value. In such a case, when the actual value drops below the reference value after having been above the reference value, the controller causes the device to switch from a condition for directing the flow of breast milk to the destination position A to a condition for directing the flow of breast milk to the destination position B, without any need for intervention of the user of the breast pump device.

In a practical embodiment, the breast pump device according to the invention comprises at least two connection arrangements allowing for connection of at least two receptacles for receiving breast milk to the device, and a separation unit for allowing milk to flow to a connected receptacle through at least one of the at least two connection arrangements and for preventing milk to flow to a connected receptacle through at least one other of the at least two connection arrangements. By having the two connection arrangements and the separation unit as mentioned, it is very well possible to realize the desired result, i.e. the at least two batches of breast milk as a result of a single pumping session on at least one user's breast. All that needs to be done is connecting at least two receptacles to the breast pump device through the connection arrangements, wherein a flow of milk is directed to one of the two receptacles as long as it is found that the actual value of the at least one quality parameter of the milk is at one side of the reference value, and wherein the flow of milk is directed to the other of the two receptacles as soon as it appears that the actual value of the at least one quality parameter of the milk passes from the one side of the reference value to the other. In that case, it is practical for the controller to be adapted to set a condition of the separation unit. For the sake of completeness, it is noted that the receptacles may be provided as separate objects such as separate bottles, but may also be provided in the form of separate spaces in a single receptacle unit, for example.

The separation unit may be of any suitable design for allowing a flow change from one connection arrangement to another. For example, the separation unit may comprise a valve which is movable between a first position for closing one of the connection arrangements while leaving the other of the connection arrangements open and a second position for closing the other of the connection arrangements while leaving the one of the connection arrangements open.

It is possible for the breast pump device according to the invention to comprise an information unit for providing real-time information about the at least one quality parameter to the user of the device. In that case, a user is assisted in interpreting operational aspects of the device, which may be beneficial to the user's perception of quality and reliability of the device. Such information unit may further be adapted to issue a warning signal to the user in case the actual value of the at least one quality parameter passes from one side of the reference value to the other, so that the user may be alerted to the situation in which the path followed by the milk is changed.

A practical example of the at least one milk quality parameter is milk fat concentration. Hence, the detection unit may be adapted to detect milk fat concentration, and may particularly be adapted to do so on the basis of a light scattering measurement technique such as infrared spectroscopy or near infrared spectroscopy, which does not alter the fact that within the framework of the invention, other suitable measurement techniques may be applied as well.

In order to allow for flexible use of the breast pump device, it is advantageous if the device is equipped with a user interface for allowing a user to set the reference value of the at least one quality parameter of the breast milk. Also, in case the detection unit is adapted to detect more than one type of quality parameter, having a user interface is a feasible option for allowing a user to choose the type of quality parameter, and to possibly also set the reference value of that particular parameter. Having a user interface further allows for offering a user the option of operating the breast pump device in a conventional manner, in a default setting in which the detection unit is not used, when there is no need for separating a total volume of milk to be extracted from a breast in at least two different batches. The controller may be equipped with a programmable memory for storing input as provided by a user.

The above-described and other aspects of the invention will be apparent from and elucidated with reference to the following detailed description of two embodiments of a breast pump device comprising a detection unit and a controller for controlling operation of the device on the basis of the detection results provided by the detection unit.

BRIEF DESCRIPTION OF THE DRAWINGS

The invention will now be explained in greater detail with reference to the figures, in which equal or similar parts are indicated by the same reference signs, and in which.

DETAILED DESCRIPTION OF THE EMBODIMENTS

Figure 1:
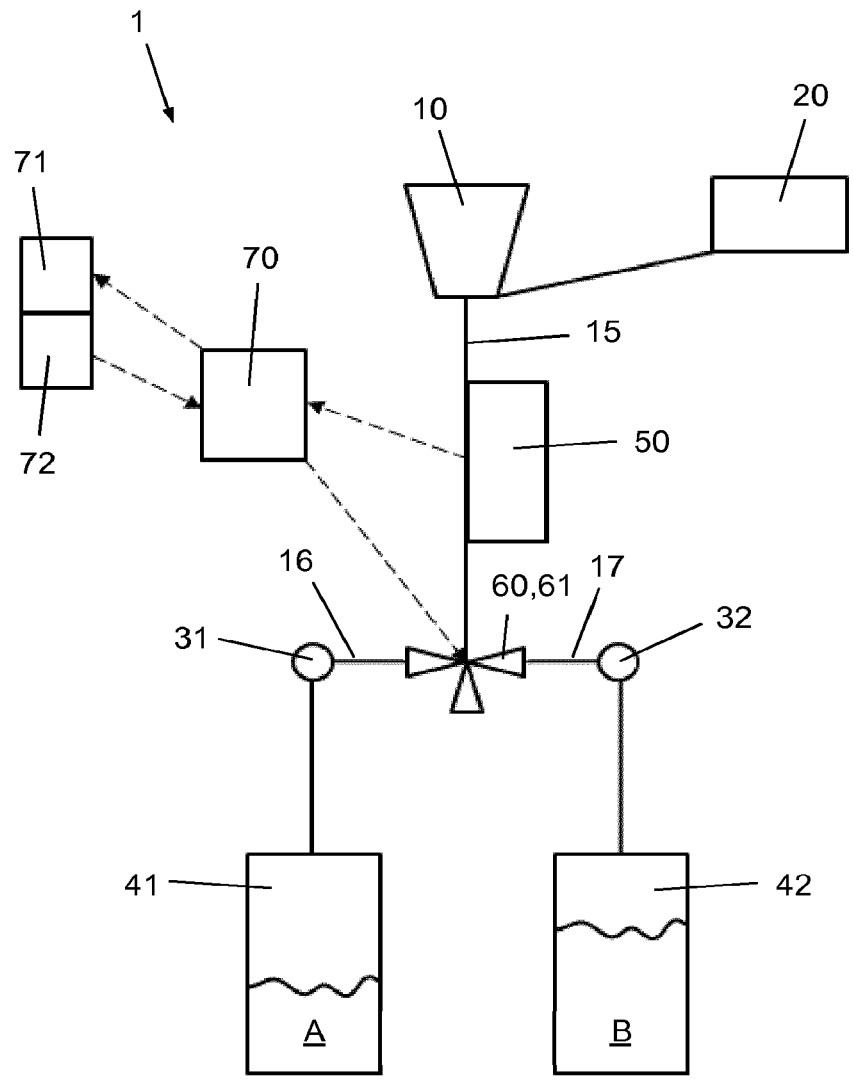
FIG. 1 diagrammatically shows components of a first embodiment of the breast pump device according to the invention, which is suitable to be used for extracting milk from one breast, and also diagrammatically shows two receptacles connected to the breast pump device.
Figure 2:
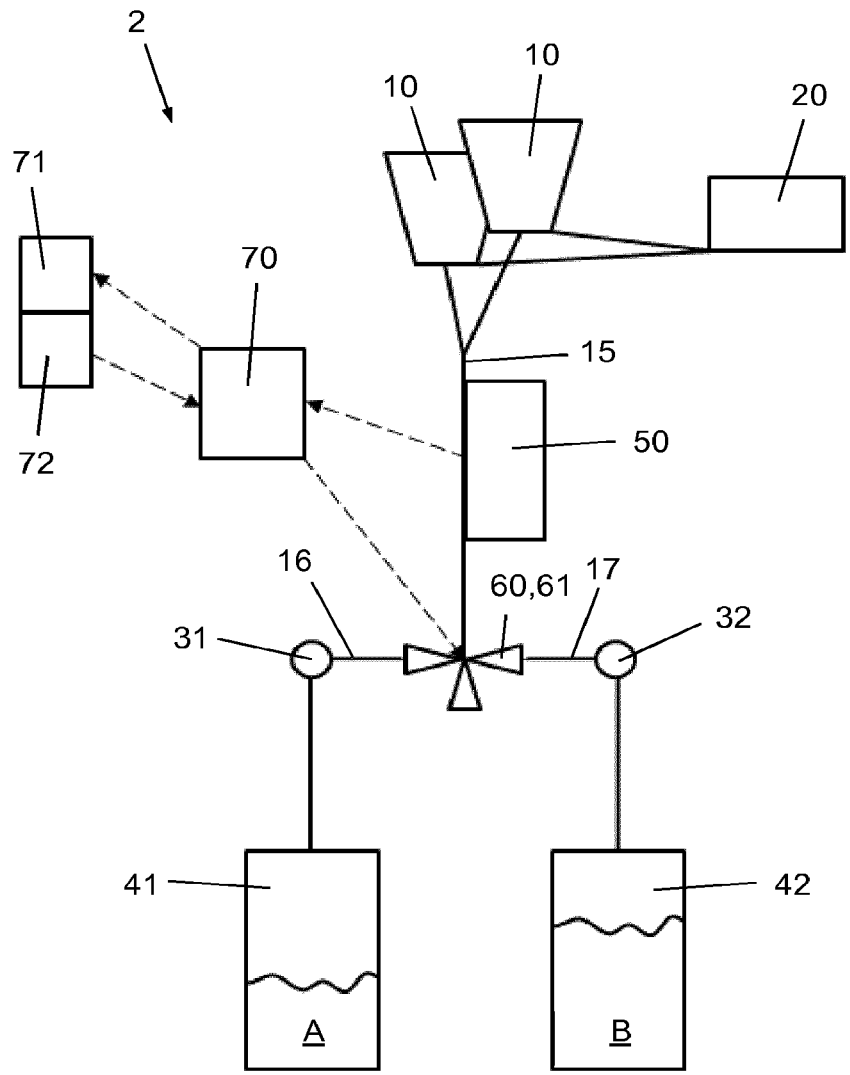
FIG. 2 diagrammatically shows components of a second embodiment of the breast pump device according to the invention, which is suitable to be used for extracting milk from two breasts at the same time, and also diagrammatically shows two receptacles connected to the breast pump device.

FIGS. 1 and 2 diagrammatically show embodiments of a breast pump device according to the invention. The working principle of the two embodiments is comparable. The difference between the embodiments resides in the fact that the first embodiment is suitable for extracting milk from one breast, and that the second embodiment is suitable for extracting milk from two breasts at the same time. In the following, the breast pump device according to the embodiment shown in FIG. 1 will be referred to as single breast pump device 1, and the breast pump device according to the embodiment shown in FIG. 2 will be referred to as double breast pump device 2.

The general working principle of a breast pump device is well-known and will be only briefly explained here. In the first place, it is noted that a breast pump device comprises at least one funnel-shaped element for receiving a user's breast, wherein a single breast pump device comprises one such element, and wherein a double breast pump device comprises two such elements. Also, a vacuum pump is present for connection to the funnel-shaped element(s) during operation of the breast pump device. The vacuum pump may be of the manually operated type, but more sophisticated types of breast pump devices comprise an electric vacuum pump. Further, the breast pump device comprises at least one connection arrangement enabling connection of a receptacle such as a milk bottle to the device, wherein a single breast pump device comprises one such arrangement, and wherein a double breast pump device comprises one or two of such arrangements, depending on whether the funnel-shaped elements are connected to a common milk discharge line, or not.

General operational aspects of a breast pump device will now be mentioned in the context of a single breast pump. Before the vacuum pump is activated, the user needs to take care that a suitable receptacle for receiving the breast milk is connected to the breast pump device through the connection arrangement, that the vacuum pump is connected to the funnel-shaped element, and that the breast to be subjected to a milk extraction process is properly inserted into the funnel-shaped element. When, starting from that situation, the vacuum pump is activated, the breast is subjected to forces which serve for simulating a feeding situation, as a result of which milk supply is induced from the breast. The breast milk flows from the funnel-shaped element to the receptacle through the connection arrangement, under the influence of gravity and/or the vacuum. In many practical cases, the connection arrangement is present directly downstream of the funnel-shaped element, but it is also possible that a discharge tube or the like of a certain length is present, extending between the funnel-shaped element and the connection arrangement.

The invention will now be explained with reference to the schematic representations of a single breast pump device 1 in FIG. 1 and a double breast pump device 2 in FIG. 2, in which the funnel-shaped element is indicated by means of reference numeral 10 and the vacuum pump is indicated by means of reference numeral 20.

With reference to FIG. 1, it is noted in respect of the single breast pump device 1 according to the invention that this device has first and second connection arrangements 31, 32.

In the figure, it is shown how a first receptacle 41 is connected to a first connection arrangement 31, and how a second receptacle 42 is connected to a second connection arrangement 32. The first and second connection arrangements 31, 32 may comprise ends of tubes to be inserted in the respective first and second receptacles 41, 42, for example, or threaded rings to which the first and second receptacles 41, 42 may be connected by a screwing action, or any other practical means for establishing the connection of the first and second receptacles 41, 42 to the single breast pump device 1 in such a way that the first and second receptacles 41, 42 are in a position for receiving milk from the single breast pump device 1. The connections of the first and second receptacles 41, 42 to the first and second connection arrangements 31, 32 do not necessarily need to be releasable, although this is very practical. In the case of a fixed connection of the first and second receptacles 41, 42 to the first and second connection arrangements 31, 32, it is advantageous for the first and second receptacles 41, 42 to be drainable through a suitable tap or valve element, for example.

Further, the single breast pump device 1 according to the invention is equipped with a detection unit 50 for performing real-time detection of a value of at least one quality parameter of the breast milk flowing from the funnel-shaped element 10 in the direction of the first and second connection arrangements 31, 32, a separation unit 60 having a valve 61 for allowing access to only one of the first and second receptacles 41, 42 through the respective first and second connection arrangements 31, 32, and a controller 70 for controlling a condition of the separation unit 60 in dependence of the detection results yielded by the detection unit 50. The detection unit 50 is arranged upstream of the separation unit 60, and the separation unit 60 is arranged upstream of the first and second connection arrangements 31, 32. In the arrangement as described, a milk discharge line comprises three parts, namely a first part 15 extending from the funnel-shaped element 10 to the separation unit 60, a second part 16 extending from the separation unit 60 through the first connection arrangement 31, and a third part 17 extending from the separation unit 60 through the second connection arrangement 32.

In the following, by way of example, it is assumed that the detection unit 50 comprises a near infrared spectrometer which is adapted to detect milk fat concentration of a flow of milk. In that case, when the single breast pump device 1 is operated and milk is flowing through the single breast pump device 1, the detection unit 50 functions to provide real-time information about the milk fat concentration to the controller 70. This may be done in any suitable manner, on the basis of a detection signal transmitted from the detection unit 50 to the controller 70 as diagrammatically indicated through a dashed arrow in FIG. 1. The controller 70 is adapted to determine a relation between the actual value of the milk fat concentration detected by the detection unit 50 and a reference value, i.e. to determine whether the actual value is higher than, lower than or equal to the reference value. Depending on the outcome, i.e. the relation as found by the controller 70, it is known what the setting of the separation unit 60 should be on the basis of a predetermined relation between the outcome and the setting as mentioned.

It follows from the foregoing that the single breast pump device 1 according to the invention is capable of separating a total volume of breast milk as obtained during a pumping session in two batches A and B, wherein the batches A and B are different as far as the milk fat concentration is concerned. One of the batches A and B has a relatively high milk fat concentration, whereas another of the batches A and B has a relatively low milk fat concentration. The distinction between the batches A and B is determined by the reference value, and the actual creation of the different batches A and B is controlled by adapting the condition of the separation unit 60, particularly the position of the valve 61, to the outcome of a real-time comparison of an actual value of the milk fat concentration to the reference value. The action of the controller 70 in respect of setting the position of the valve 61 is diagrammatically indicated through a dashed arrow in FIG. 1.

In conformity with the aspects of the single breast pump device 1 as described in the foregoing, one feasible example of the various steps which are taken during a pumping session will now be given. According to this example, operation of the single breast pump device 1 starts with the valve 61 of the separation unit 60 being in a position for allowing access to the first receptacle 41 through the first connection arrangement 31 while blocking access to the second receptacle 42 through the second connection arrangement 32. Throughout the operation of the single breast pump device 1, the detection unit 50 and the controller 70 are in an active condition, the detection unit 50 for performing real-time measurements of the milk fat concentration of the flow of milk passing through the first part 15 of the milk discharge line, and the controller 70 for continuously determining the position of the valve 61 on the basis of the information provided by the detection unit 50 about the milk fat concentration. As long as it is found that the actual value of the milk fat concentration is lower than the reference value, the valve 61 is kept in the position as mentioned earlier, i.e. the position for allowing access to the first receptacle 41 through the first connection arrangement 31 while blocking access to the second receptacle 42 through the second connection arrangement 32. Hence, in a primary stage of the pumping session, a batch A is obtained in the first receptacle 41 on the basis of the fact that milk flows from the funnel-shaped element 10 to the first receptacle 41 via the first part 15 and the second part 16 of the milk discharge line, the batch A having a relatively low milk fat concentration.

As time passes, the milk fat concentration of the milk extracted from the breast of the user increases. As a consequence, at a certain point, it is found that the actual value of the milk fat concentration is higher than the reference value. In this situation, it is intended to separate the milk flowing from the breast from the batch A of milk which has already been connected in the first receptacle 41. This is realized on the basis of the fact that the controller 70 causes the position of the valve 61 to change, by following a predetermined relation between the position of the valve 61 on the one hand and the relation between the actual value of the milk fat concentration and the reference value on the other hand. In this way it is achieved that when the actual milk fat concentration passes from below the reference value to above the reference value, the position of the valve 61 is switched to a position for allowing access to the second receptacle 42 through the second connection arrangement 32 while blocking access to the first receptacle 41 through the first connection arrangement 31. In the second receptacle 42, a batch B of milk having a relatively high fat concentration is obtained, which is separate from the batch A of milk having a relatively low fat concentration in the first receptacle 41. Under normal circumstances, it may be expected that the value of milk fat concentration does not fluctuate around the reference value, but if it does, the separation function is always realized as the position of the valve 61 is automatically chosen in accordance with the outcome of the comparison of the actual value with the reference value.

The invention provides for an easy and a convenient way of separating one batch of breast milk from another on the basis of a difference in at least one quality parameter of the milk. The single and double breast pump devices 1, 2 according to the invention is adapted to automatically determine an appropriate destination position (e.g., first and second receptacles 41, 42) of the milk flowing through the single and double breast pump devices 1, 2 during a pumping session, on the basis of a continuous process of detecting an actual value of the quality parameter and comparing that value to a reference value, wherein the real-time relation of the actual value and the reference value determines which destination position (e.g., first or second receptacles 41, 42) is applicable at that point.

In principle, a double breast pump device according to the invention may be in fact a kind of combination of two single breast pump devices 1 as described in the foregoing, but in that case, four receptacles would be needed, two for each breast, which is an unnecessarily complex situation. Also, two detection units 50 would be needed, which would add to the costs of the device. FIG. 2 illustrates the set-up of a more practical double breast pump device 2 according to the invention. In comparison to the single breast pump device 1, there is an additional funnel-shaped element 10, which is connected to the first part 15 of the milk discharge line downstream of the detection unit 50. Apart from that, the double breast pump device 2 is comparable to the single breast pump device 1 and functions in the same manner. Besides this practical embodiment of the double breast pump device 2, a double breast pump device in which the flows of breast milk as obtained from two breasts are not merged downstream of the detection unit 50 is also covered by the invention. In the first place, the option of having a kind of combination of two single breast pump devices 1 exists, as mentioned in the foregoing. In that case, the breast pump device comprises two milk discharge lines, two detection units 50, two separation units 60, and four connection arrangements 31, 32. In the second place, it is possible to have a double breast pump device which is equipped with two detection units 50 or a detection unit 50 which is adapted to perform measurements at two different positions in the device, and two separation units 60, wherein each of the separation units 60 is associated with the same first and second connection arrangements 31, 32, in which case only the first and second connection arrangements 31, 32 and consequently first and second receptacles 41, 42 are needed. In a double breast pump device comprising two detection units 50 or a detection unit 50 which is adapted to perform measurements at two different positions in the device, it is possible to apply the quality requirements of the breast milk to the milk of two breasts separately, which guarantees a collection of a maximum quantity of milk meeting the quality requirements.

FIGS. 1 and 2 further illustrate the option of having an information unit in the single and double breast pump devices 1, 2 according to the invention for providing real-time information about the at least one quality parameter to the user of the single and double breast pump devices 1, 2, the information unit being diagrammatically depicted by means of an information unit 71, and a dashed arrow indicating a connection of the information unit 71 to the controller 70. Further, FIGS. 1 and 2 illustrate the option of having a user interface for allowing a user to set the reference value of the at least one quality parameter, the user interface being diagrammatically depicted by means of a user interface 72, and a dashed arrow indicating a connection of the user interface 72 to the controller 70.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

Summarizing, the invention relates to a single breast pump device 1 and a double breast pump device 2, which are adapted to enable realization of at least two batches A, B of breast milk as a direct result of a single pumping session to be performed on at least one user's breast, which batches A, B are different as far as the value of at least one quality parameter of the breast milk is concerned, and which batches A, B are realized at different destination positions (e.g., first and second receptacles 41, 42). The single and double breast pump devices 1, 2 comprises a detection unit 50 for performing real-time detection of the at least one quality parameter in a flow of breast milk and outputting a detection signal representing an actual value of the at least one quality parameter, and further comprises a controller 70 for receiving the detection signal from the detection unit 50 and using the signal in a process of determining an appropriate setting of the single and double breast pump devices 1, 2 as far as the choice of a destination position (e.g., first or second receptacles 41, 42) of the milk is concerned.

The invention claimed is:

1. A method of providing at least two batches of breast milk from a single pumping session from a breast pump device, the at least two batches differing in at least one quality parameter of the breast milk, the method comprising:
    performing real-time detection of the at least one quality parameter in a flow of breast milk extracted during a pumping session, wherein the at least one quality parameter comprises milk fat concentration, or protein content, or both;
    outputting a detection signal representing an actual value of the at least one quality parameter;
    receiving the detection signal;
    determining in real-time a relation between the actual value of the at least one quality parameter and a reference value; and
    controlling the breast pump device to direct the flow of breast milk to a destination position based on the relation.

2. The method according to claim 1, further comprising:
    connecting at least two receptacles to receiving breast milk to the breast pump device; and
    separating the breast milk to flow to one of the at least two of the at least two receptacles through at least one of at least two connection arrangements; and
    preventing the breast milk from flowing to the other of the at least two receptacles through at least one other of the at least two connection arrangements, wherein the at least two connection arrangements each comprise ends of tubes to be inserted respectively in the at least two receptacles.

3. The method according to claim 2, further comprising:
    moving a valve between a first position for closing one of the at least two connection arrangements while leaving the other of the at least two connection arrangements open, and a second position for closing the other of the at least two connection arrangements while leaving the one of the at least two connection arrangements open, wherein the at least two connection arrangements each comprise ends of tubes to be inserted respectively in the at least two receptacles.

4. The method according to claim 2, further comprising providing real-time information about the at least one quality parameter.

5. The method according to claim 4, further comprising issuing a warning signal when the actual value of the at least one quality parameter passes from below the reference value to above the reference value or from above the reference value to below the reference value.

6. The method according to claim 1, further comprising detecting a milk fat concentration.

7. The method according to claim 6, wherein the detecting the milk fat concentration further comprises measuring light scattered from the breast milk.

8. A breast pump device, adapted to provide at least two batches of breast milk from a single pumping session, the at least two batches differing in at least one quality parameter of the breast milk, the breast pump device comprising:
    an infrared or near-infrared spectrometer adapted detect a milk fat concentration,
    a non-transitory computer-readable storage medium having stored therein machine readable instructions; and
    a controller configured to execute the instructions retrieved from the non-transitory computer-readable storage medium, wherein the instructions, when executed, cause the controller to:
    receive a detection signal representing an actual value of the at least one quality parameter;
    determine, in real-time, a relation between the actual value of the at least one quality parameter and a reference value; and
    control the breast pump device to direct flow of the breast milk to a destination position based on the relation.

9. The breast pump device according to claim 8, further comprising:
- at least two connection arrangements adapted to connect at least two receptacles for receiving breast milk to the breast pump device; and
- a valve adapted to allow the breast milk to flow to one of the at least two of the at least two receptacles through at least one of the at least two connection arrangements, and to prevent milk from flowing to the other of the at least two receptacles through at least one other of the at least two connection arrangements, wherein the at least two connection arrangements each comprise ends of tubes to be inserted respectively in the at least two receptacles.

10. The breast pump device according to claim 9, the controller being configured to execute the instructions retrieved from the non-transitory computer-readable storage medium, wherein the instructions, when executed, further cause the controller to adapted to set a condition of the valve.

11. The breast pump device according to claim 8, further comprising:
- at least two connection arrangements adapted to connect at least two receptacles for receiving breast milk to the breast pump device; and
- a valve adapted to allow the breast milk to flow to one of the at least two of the at least two receptacles through at least one of the at least two connection arrangements, and to prevent milk from flowing to the other of the at least two receptacles through at least one other of the at least two connection arrangements, wherein the at least two connection arrangements each comprise ends of tubes to be inserted respectively in the at least two receptacles.

12. The breast pump device according to claim 11, wherein the controller is adapted to set a condition of the valve.

13. The breast pump device according to claim 11, wherein the valve is movable between a first position for closing one of the at least two connection arrangements while leaving the other of the two connection arrangements open, and a second position for closing the other of the two connection arrangements while leaving the one of the at least two connection arrangements open.

14. The breast pump device according to claim 8, further comprising a computer adapted to provide information about the at least one quality parameter.

15. The breast pump device according to claim 14, the computer being adapted to issue a warning signal when the actual value of the at least one quality parameter passes from below the reference value to above the reference value or from above the reference value to below the reference value.

16. The breast pump device according to claim 8, further comprising a user interface adapted to allow a user to set the reference value of the at least one quality parameter.

17. The breast pump device according to claim 16, wherein the instructions, when executed, cause the controller to determine whether the actual value of the milk fat concentration is higher than, lower than or equal to the reference value.

18. The breast pump device according to claim 17, further comprising a valve, wherein the instructions, when executed, cause the controller to determine a setting of the based on a predetermined relation between an outcome and the setting.

19. The breast pump device according to claim 18, wherein a unit is adapted to separate a total volume of breast milk as obtained during a pumping session into two batches, wherein the two batches differ in milk at concentration.

20. The breast pump device according to claim 8, wherein the infrared or near-infrared spectrometer is adapted to perform measurements at two different positions in the breast pump device.

* * * * *